United States Patent [19]
Kaganov et al.

[11] Patent Number: 5,876,367
[45] Date of Patent: Mar. 2, 1999

[54] CEREBRAL PROTECTION DURING CAROTID ENDARTERECTOMY AND DOWNSTREAM VASCULAR PROTECTION DURING OTHER SURGERIES

[75] Inventors: Alan L. Kaganov, Portola Valley; Jonathan D. Root, San Francisco; John McKenzie, San Carlos, all of Calif.

[73] Assignee: Embol-X, Inc., Portola Valley, Calif.

[21] Appl. No.: 759,591

[22] Filed: Dec. 5, 1996

[51] Int. Cl.$^6$ ........................................ A61M 5/00
[52] U.S. Cl. ........................ 604/8; 606/200; 606/159
[58] Field of Search ........................... 606/200, 159; 604/8, 9, 284

[56] References Cited

U.S. PATENT DOCUMENTS

| | | | |
|---|---|---|---|
| 3,435,824 | 4/1969 | Gamponia ................................. | 604/8 |
| 4,596,557 | 6/1986 | Pexa ....................................... | 604/284 X |
| 4,661,110 | 4/1987 | Fortier et al. ........................... | 604/284 X |
| 4,873,978 | 10/1989 | Ginsburg . | |
| 5,273,533 | 12/1993 | Bonaldo ................................. | 604/284 X |
| 5,328,480 | 7/1994 | Melker et al. .......................... | 604/284 X |
| 5,591,128 | 1/1997 | Sithole .................................. | 604/284 X |
| 5,632,735 | 5/1997 | Wyatt et al. ............................. | 604/283 |

OTHER PUBLICATIONS

Loftus, *Carotid Endarterectomy Principles and Technique*, Quality Medical Publishing, Inc., St. Louis, Missouri, Editor B. Campbell (1995).

Smith, "The Surgical Treatment of Peripheral Vascular Disease," Chapter 142, Part VIII, Techniques of Special Procedures, p. 2233.

Barbut et al *Cerebral Emboli Detected During Bypass Surgery Are Associated with Clamp Removal*, Stroke vol. 25 No. 12 (Dec. 1994) pp. 2398–2402.

*Primary Examiner*—Michael H. Thaler
*Attorney, Agent, or Firm*—Lyon & Lyon LLP

[57] ABSTRACT

A shunt and method of use for maintaining distal blood flow during an arteriotomy procedure is disclosed. The shunt includes a first tubular member having a proximal end, a distal end, and a lumen therebetween. The proximal end has an opening in communication with the lumen, and the proximal opening is adapted to receive blood from a first region of an artery. The distal end has an opening in communication with the lumen, and the distal opening is adapted to release blood into a second region of the artery. The shunt includes a second tubular member having a proximal end, a distal end, and a lumen therebetween which either merges and communicates at its distal end with the lumen of the first tubular member, or rides separate and parallel to it. The shunt also includes a hemostatic valve attached to the proximal end of the second tubular member, the valve acting to prevent loss of blood from the lumen of the second tubular member and to permit the introduction of a medical device into the lumen of the second tubular member and into the artery. In use, the distal opening of the shunt is inserted into the second region of an artery and secured to the lumen of the artery. A blood filter device is deployed within the artery. The proximal opening of the shunt is inserted into the first region of the artery and secured to the lumen of the artery. Endarterectomy is performed on the region of the artery which lies between the proximal opening and the distal opening of the shunt, and embolic material dislodged during the procedure is captured by the filter.

17 Claims, 4 Drawing Sheets

5,876,367

CEREBRAL PROTECTION DURING CAROTID ENDARTERECTOMY AND DOWNSTREAM VASCULAR PROTECTION DURING OTHER SURGERIES

FIELD OF THE INVENTION

This invention relates to carotid endarterectomy surgery. More particularly, it relates to methods and apparatus for improving endarterectomy procedures by using blood filtration to protect the patient from embolization during these vascular surgeries.

BACKGROUND OF THE INVENTION

Endarterectomy is a surgical procedure which generally includes the removal of the lining of an artery. Typically the artery is dissected longitudinally to expose an affected region from which plaque and other materials may be removed. Endarterectomy can be performed on almost any major artery that is diseased or blocked, and is most commonly used for the carotid, femoral, and popliteal arteries.

In a typical procedure, the surgeon makes a standard vertical incision in the neck of a patient, or a transverse incision corresponding to a skin line of the neck. The incision is deepened through and around subcutaneous adipose tissue, platysma muscle, the branches of the external jugular vein, and the border of the sternocleidomastoid muscle in order to expose the carotid sheath. Careful dissection is used to expose the common carotid artery and its external and internal branches. Vascular clamps are applied to the internal carotid artery, external carotid artery, and common carotid artery, and a vertical arteriotomy is made in the common carotid artery, typically below the bifurcation. The incision may be advanced into the internal carotid artery to a point beyond the area which contains plaque material.

An indwelling shunt may then be installed in order to bypass the clamped region of the artery so that brain perfusion is not disrupted. The artery is then clamped proximal and distal about the shunt in order to isolate a bloodless region for endarterectomy. Atheromatous material is then removed, first from the common carotid artery, then from the external carotid artery, and generally last from the internal carotid artery. After the endarterectomy procedure has been performed, the surgeon cleans the region of plaque fragments before removal of the shunt and closure of the vascular incision.

The above-described procedure, however, suffers from a deficiency which relates to the escape of embolic material which may lead to devastating neurologic complications, particularly when emboli escape through the internal carotid artery. Emboli may be produced through any step of the procedure where mechanical forces are applied to the artery, and these manipulations include clamping, unclamping, applying a tourniquet, dissecting the vessel, inserting and removing a bypass shunt, removing atheromatous material, cleaning the affected site, and suturing the vessel. Therefore, a need exists for an improved endarterectomy procedure and apparatus which will enable the surgeon to minimize the production of embolic material and to prevent the escape of embolic material during carotid endarterectomy, arteriotomy, and other vascular surgeries.

SUMMARY OF THE INVENTION

A dramatic improvement in the neurologic outcome of patients undergoing carotid endarterectomy, and arteriotomy procedures generally, can be achieved by using a blood filter device to capture and remove dislodged embolic material during the surgical procedure in accordance with our invention. Thus, the invention provides novel methods and apparatus for protecting a patient from embolization during arteriotomy procedures. In one embodiment, the invention provides a bypass tubing or indwelling shunt, having a main lumen for blood bypass and a second, branching lumen adapted to receive an elongated blood filtration instrument, or other surgical device (e.g., an angioplasty catheter, stent catheter, atherectomy catheter) and to allow passage of same into an artery distal to the endarterectomy region. The branching secondary lumen can either merge and communicate with the main lumen of the shunt, or may extend to a distal opening separate from the blood bypass lumen of the device.

In another embodiment, a standard single-lumen indwelling shunt is used in accordance with the disclosure of Loftus, *Carotid Endarterectomy Principles and Techniques;* Quality Medical Publishing, Inc.: St. Louis, Mo., 1995 (this and all other references cited herein are expressly incorporated by reference as if fully set forth in their entirety herein), and an introducer sheath and filtration catheter are provided for deployment distal to the site of standard carotid endarterectomy. The introducer sheath includes a hemostatic valve adapted to receive a filtration catheter. The filtration catheter typically includes a catheter sheath, an elongated control member, a control mechanism at a proximal end of the control member, and a filtration assembly which includes an expansion frame and filter mesh at a distal region of the control member, the expansion frame being operable to enlarge from a contracted condition to an expanded condition which covers all of, or a substantial portion of the cross-sectional area of a vessel. In alternative embodiments, a filter is disposed on a guidewire or tubing for use in carotid artery bypass to capture clots and atherosclerotic material released during endarterectomy.

According to the methods of the present invention, an affected region of an artery is isolated, clamped, and dissected as disclosed in Loftus, *Carotid Endarterectomy Principles and Techniques;* Quality Medical Publishing, Inc.: St. Louis, Mo., 1995, and Smith, *The Surgical Treatment of Peripheral Vascular Disease,* Chapter 142, in "The Heart, Arteries, and Veins," Vol. 2, Ed. J. Willis Hurst; McGraw-Hill Information Services Corp., 1990. An indwelling shunt as described herein is then inserted so that the distal region penetrates into the distal artery and is secured by a distal artery clamp, while the proximal region penetrates into the proximal artery and is secured by a clamp proximal to the region of arteriotomy. A blood filter device is deployed through the second lumen of the indwelling shunt as disclosed herein, is advanced within the blood vessel, and then expanded to cover a substantial cross-sectional area of the artery distal to the arteriotomy region. Endarterectomy is performed in accordance with standard procedures to remove atherosclerotic material from the affected region of the artery.

According to an alternative method, a non-indwelling shunt or plastic tubing as disclosed herein is used to bypass an affected region of the artery. After the carotid artery is exposed, an incision is made proximal to the site where the common carotid artery cross-clamp will be placed. Plastic tubing having an appropriate size is placed in this incision and then extended distally, past the site where the internal carotid artery cross-clamp will be placed, and distal to the atherosclerotic plaque, where the plastic tubing reenters the carotid artery through a second incision. A filter device is deployed in the internal carotid artery through a side-port on the shunt, or the filter may be deployed by an expansion mechanism intrinsic to the tubing itself. The common and internal carotid arteries are then clamped. The carotid artery is incised, plaque removed, the operative site rinsed with sterile saline or water, and the carotid artery, with or without a graft, is closed. The proximal and distal cross-clamps are removed, and circulation through the repaired carotid artery is restored as discussed herein. The proximal end of the plastic tubing is removed from the common carotid artery and the proximal incision is closed. The filter, including captured embolic material, is retracted after several minutes, typically at least 5 minutes, more preferably at least 10 minutes, and the distal end of the shunt is removed. Finally, the distal incision is closed.

BRIEF DESCRIPTION OF THE DRAWINGS

FIG. 3A is a cross-sectional view taken through section line 3A—3A of the shunt and vessel depicted in FIG. 3;

FIG. 6 depicts an indwelling common lumen shunt and filter deployed within an artery during an endarterectomy procedure.

DETAILED DESCRIPTION OF THE INVENTION

The devices and methods disclosed herein function to prevent embolic material from migrating downstream (into the brain, organs, extremities of the limbs, etc.) during vascular surgery. The devices and methods herein are useful during any procedure where vessels are cut open for the purpose of removing occlusions or performing other types of repair that may require the use of shunting to maintain distal blood flow.

Figure 1:
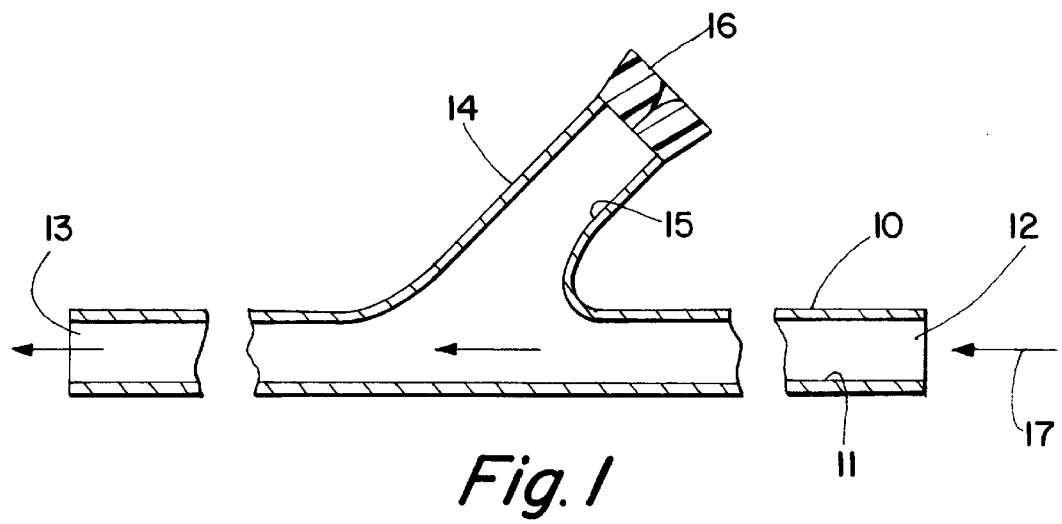
FIG. 1 depicts a common or merging lumen shunt in accordance with one embodiment of the present invention.

According to one embodiment, the shunt is as depicted in FIG. 1. The shunt includes elongated tubular member 10 having lumen 11 which extends from proximal opening 12 to distal opening 13. Within an intermediate section of tubular member 10, the shunt includes a "Y" arm, or second tubular member 14 having lumen 15 which branches away from main lumen 11. Thus, at one end, lumen 15 merges and communicates with lumen 11, while at the other end, lumen 15 terminates at hemostatic valve 16 which permits device introduction. The direction of blood flow through the shunt during use is depicted by arrow 17. The "communicating lumen" shunt as depicted in FIG. 1 will typically be constructed from a very soft, atraumatic material, e.g., silicon, latex, urethane. The length of tubular member 10 from its proximal opening to its distal opening will typically be greater than 5 cm, more typically greater than 8 cm, more typically greater than 10 cm, more typically greater than 12 cm, more typically 15 cm or more in length. Meanwhile, the outer diameter of tubular member 10 will generally be 3 mm or greater, more generally 4 mm or greater, more generally 5 mm or greater. The foregoing ranges are set forth solely for the purpose of illustrating typical device dimensions. The actual dimensions of a device constructed according to the principles of the present disclosure may obviously vary outside of the listed ranges without departing from those basic principles disclosed herein.

Figure 2:
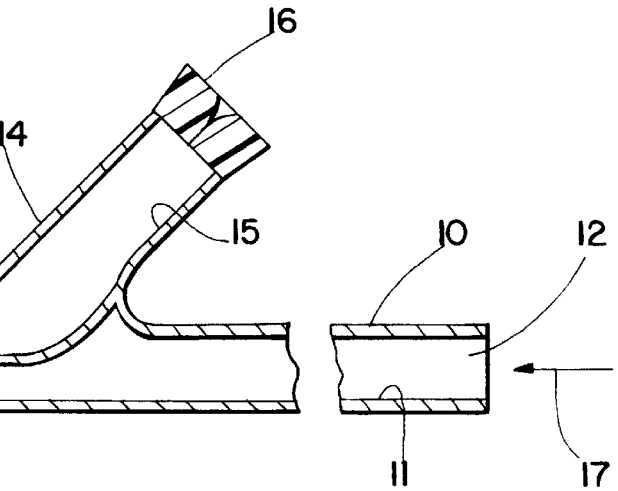
FIG. 2 depicts a non-communicating lumen shunt in accordance with another aspect of the present invention.

In a second embodiment, the shunt includes elongated tubular member 10 with lumen 11 as depicted in FIG. 2. A second tubular member 14 is provided having lumen 15 extending from hemostatic valve 16 at a proximal end to opening 18 at a distal end thereof. Lumen 15 therefore includes a first segment which runs substantially parallel to lumen 11 of main tubular member 10, and a second segment which branches away from lumen 11 and terminates proximally at hemostatic valve 16. This "non-communicating lumen" shunt allows blood to flow in the direction of arrow 17 when the shunt is in use, and this shunt is constructed from the materials and according to the device parameters given above.

Figure 3:
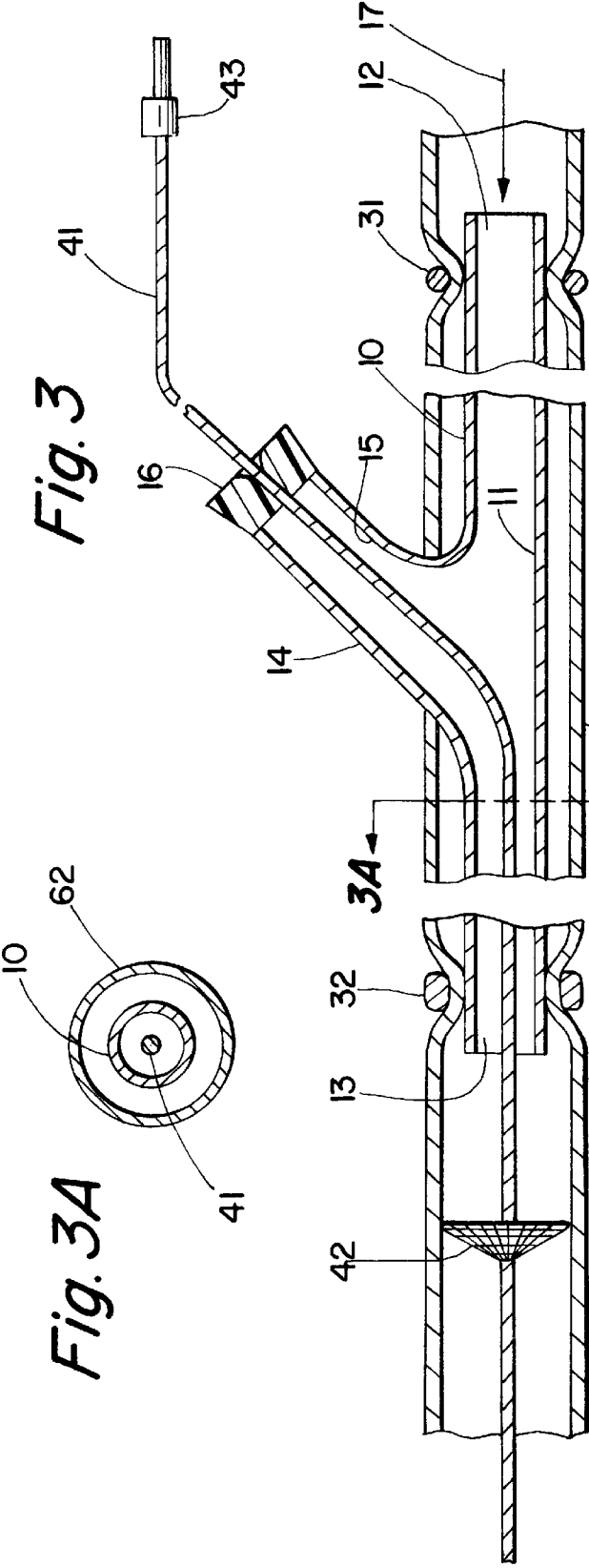
FIG. 3 depicts an indwelling common lumen shunt and filter deployed within an artery during an endarterectomy procedure.

In use, it will be understood that secondary lumen 15 defines a passageway for introduction of a medical instrument, e.g., a blood filter device, within an artery during an arteriotomy or endarterectomy procedure. With reference to FIG. 3, the use of a shunt as disclosed herein will be described in the context of an endarterectomy procedure. A typical site of atherosclerotic plaque build-up is in the common carotid artery near the segment which branches to the internal carotid artery and external carotid artery. Segment 62 of artery 61 having plaque build-up is located and exposed through an incision made in the neck of a patient. Tourniquet 31 (Rummel tourniquet) is placed loosely around the common carotid artery. A Bulldog clamp (not shown) is then secured on the internal carotid artery. Next, a DeBakey clamp (not shown) is placed on the common carotid artery proximal (upstream) of the tourniquet. The external carotid artery (not shown) is secured with a Bulldog clamp. This order of vessel clamping is significant because the clamp on the internal carotid artery is effective to catch any embolic debris dislodged by the DeBakey clamp placed on the common carotid artery.

With the clamps in place, the surgeon makes a longitudinal incision in the artery using scissors to expose the region of the artery containing plaque material. A shunt as depicted in FIG. 1 or FIG. 2 is gripped with forceps in the distal region. A second forceps is secured to the proximal region of the shunt to prevent blood escape. The Bulldog clamp which secures the internal carotid artery is loosened to allow back-bleeding while the distal opening 13 of shunt 10 is advanced distally into the internal carotid artery. When the shunt has been successfully placed in the internal carotid artery, it is secured by Javid clamp 32 to prevent further back-bleeding. It should be noted that during advancement of the distal opening of the shunt into the internal carotid artery, care must be taken to avoid scraping and thereby dislodging debris from the walls of the vessel. For this reason, the clamp on the internal carotid artery is loosened and allowed to back-bleed during the process so that antegrade blood flow blows the vessel walls apart so that tubular member 10 can be advanced through the center.

The second forceps secured to the proximal region of the shunt is released in order to vent air from the interior lumen of the shunt. A blood filter device is deployed through the hemostatic valve and advanced through lumen 15 into common lumen 11 and through distal opening 13 into artery 61. The blood filter device will typically include an elongated member 41 (guidewire, sheath, etc.) having a proximal end with control mechanism 43 for activating the filter, and filtration mesh 42 suspended on an expansion frame disposed about the distal end of elongated member 41. The construction and use of expansion frame, associated filter mesh 42, and control mechanism 43 have been thoroughly discussed in earlier applications including Barbut et al., U.S. application Ser. No. 08/553,137, filed Nov. 7, 1995, now abandoned Barbut et al., U.S. application Ser. No. 08/580,223, filed Dec. 28, 1995, now abandoned Barbut et al., U.S. application Ser. No. 08/584,759, filed Jan. 9, 1996, now abandoned Barbut et al., U.S. application Ser. No. 08/640,015, filed Apr. 30, 1996, now U.S. Pat. No. 5,769,816, Barbut et al., U.S. application Ser. No. 08/645,762, filed May 14, 1996, and Barbut et al., U.S. application Ser. No. 08/683,503, filed Jul. 17, 1996, now U.S. Pat. No. 5,662,671 and the contents of each of these prior applications are incorporated herein by reference in their entirety. It will be understood that the design and use of a filter mesh, associated expansion frame, and control mechanism as discussed in these applications is fully applicable to the use of such filter and expansion frame on a guidewire or arterial catheter system as disclosed herein.

The filter is maintained in a contracted state during entry through lumen 15, and lumen 11. Once the filter has been advanced beyond distal opening 13 of shunt 10, filter 42 is expanded to an enlarged diameter which covers a substantial portion of the cross-sectional area of vessel 61. Filter 42 is maintained in place during the remaining surgery in order to capture embolic material dislodged during the procedure.

Next, the proximal opening of the shunt is advanced proximally into the common carotid artery until it abuts against the DeBakey clamp. Tourniquet 31 is tightened and the DeBakey clamp released to allow the surgeon to slide the shunt further proximal. Once the shunt and filter are in place and operational as depicted in FIG. 3, it is generally desirable to evaluate shunt function using a Doppler probe. An audible flow signal will typically confirm patency. FIG. 3A shows a cross-sectional view of shunt 10 and elongate member 41 within vessel segment 62, taken through section line 3A—3A. The endarterectomy procedure is then performed within the dissected region of the artery. The plaque or atheroma material typically has the consistency of a thick shell. This material is dissected and peeled out of the vessel, preferably in one or a small number of large pieces. Such a monolithic removal is preferred to breaking of the plaque into small pieces as the latter may be lost in the circulation and result in emboli.

The dissected vessel is then closed by suturing both ends of the slit toward the center until a small hole remains in the common carotid artery, as described in Loftus, *Carotid Endarterectomy Principles and Techniques;* Quality Medical Publishing, Inc.: St. Louis, Mo., 1995. The shunt is then gripped by two clamps spaced by a short distance. Filter mesh 42 is contracted to a small diameter, holding captured embolic material trapped within the mesh. The filter is then withdrawn from vessel 61 into lumen 11, and then into lumen 15 and removed from hemostatic valve 16. The shunt is cut by scissors between the clamps. Both resulting pieces of the shunt are removed from the common carotid artery.

The clamp on the internal carotid artery is briefly loosened and allowed to back-bleed in order to purge air from the dissected region 62 of vessel 61. The clamp on the external carotid artery is similarly loosened briefly to back-bleed and purge air from the affected segment of the external carotid artery. The surgeon checks for thrombi enclosed within the affected segment 62 of vessel 61, and for inadvertent closure from the suture line having caught an unintended portion of the back of the vessel. Heparinized saline is injected into the small opening which remains. The last suture is tied to completely close the incision in the dissected region of vessel 61. The clamp on the external carotid artery is removed, and the clamp on the common carotid artery is removed. After a delay of 10 seconds, the clamp on the internal carotid artery is removed. This sequence ensures that any inadvertent debris or air is flushed to the external carotid artery rather than the internal carotid artery and the patient thereby avoids neurologic harm.

In another embodiment, the shunt is secured to the vessel walls using one or more balloon occluders as depicted in FIG. 6. The use of balloon occlusion eliminates the need to apply compressive clamps (numerals 31 and 32 in FIG. 3) to secure the shunt within the vessel, and thereby reduces the risk of debris dislodgement during shunt installation. With reference to FIG. 6, shunt 10 includes one or more balloon occluder 35 at its proximal and/or distal ends, the balloon occluder being disposed circumferentially around the tubing of the shunt. Occluder 35 is in fluid communication with inflation lumen 37, inflation port 38, and optionally tubing 39 for saline injection. Thus, in use, the proximal or distal end of the shunt is positioned as described above, while occluder 35 is in a deflated state. Saline, or other biotolerable fluid, is injected through port 38 until occluder 35 enlarges into contact with the inner diameter of vessel 61, thereby sealing the vessel from blood flow. A cuff or C-clamp 36 may be fitted about the vessel to prevent hyperexpansion, minimize internal slippage of the balloon occluder, and provide a tight seal within the vessel. After the endarterectomy procedure, saline is withdrawn to deflate occluder 35 before the shunt is removed from the vessel.

Figure 4:
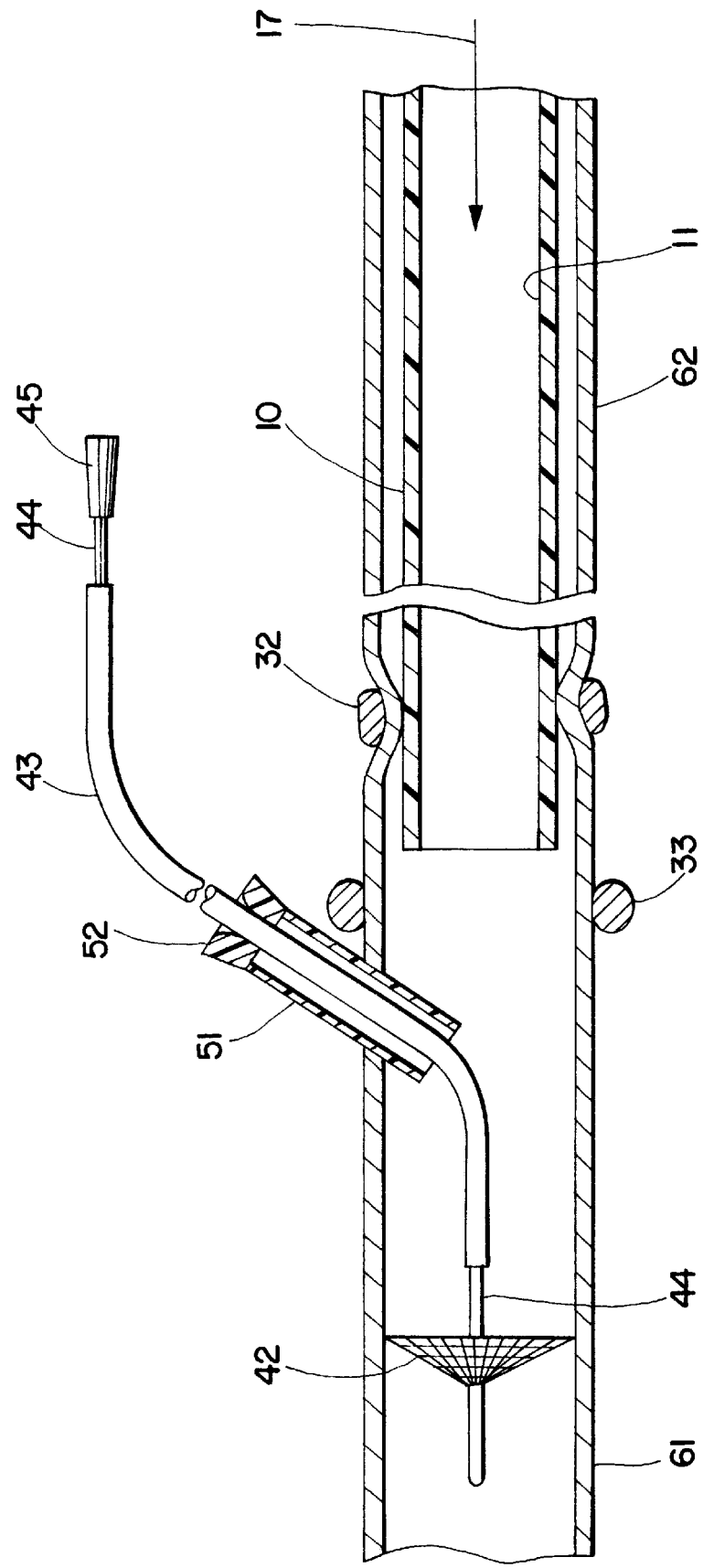
FIG. 4 depicts a standard indwelling shunt during endarterectomy and a filtration catheter deployed through an introducer sheath.

In another embodiment, the shunt and filtration assembly are separated from another as depicted in FIG. 4. Deployment of the filtration assembly makes use of introducer sheath 51 having hemostatic valve 52 at one end thereof. Introducer sheath 51 is inserted through an incision in the wall of artery 61 downstream or distal to the site of arteriotomy 62. Introducer 51 is shaped to receive catheter sheath 43 which receives elongate member 44 having filter mesh 42 operably disposed at a distal region thereof. Expansion and contraction of filter 42 is controlled by mechanism 45 which operates at the proximal region of elongate member 44. Thus, in use, after the artery is selected and isolated, introducer 51 is inserted through an incision created in the wall of artery 61. Filter catheter 43 is inserted through hemostatic valve 52 and into the lumen of vessel 61 with filtration assembly 42 being in a contracted condition. Once in place, control mechanism 45 is operated to expand filter 42 so that it covers most, if not all, of the cross-sectional area of vessel 61. With the filter in place, an endarterectomy procedure, which includes steps of clamping (using Bulldog clamp 32 and optionally vascular occlusion clamp 33), installation of a normal shunt, arteriotomy, shunt removal, and unclamping, is conducted in accordance with the description given above. Thereafter, filter 42 is contracted and removed from artery 61 through introducer 51. In a final step, introducer 51 is removed from the artery and the opening in artery 61 is sutured.

It will be understood that the ordering of steps can be modified so that introduction of filter 42 may occur at any point in the procedure. However, in a preferred embodiment, the filter is deployed before arteriotomy begins and the filter is removed after arteriotomy has been completed. In this manner, filter 42 is available to capture all embolic material which results from the manipulative steps of the arteriotomy procedure, e.g., clamping, unclamping, installation of tourniquet, installation and movement of shunt 10, cutting of vessel 61, suturing the vessel, and shunt removal. Thus, the method depicted in FIG. 4 constitutes a preferred embodiment insofar as it allows the surgeon to maintain filter 42 deployed within the vessel throughout the arteriotomy procedure.

Figure 5:
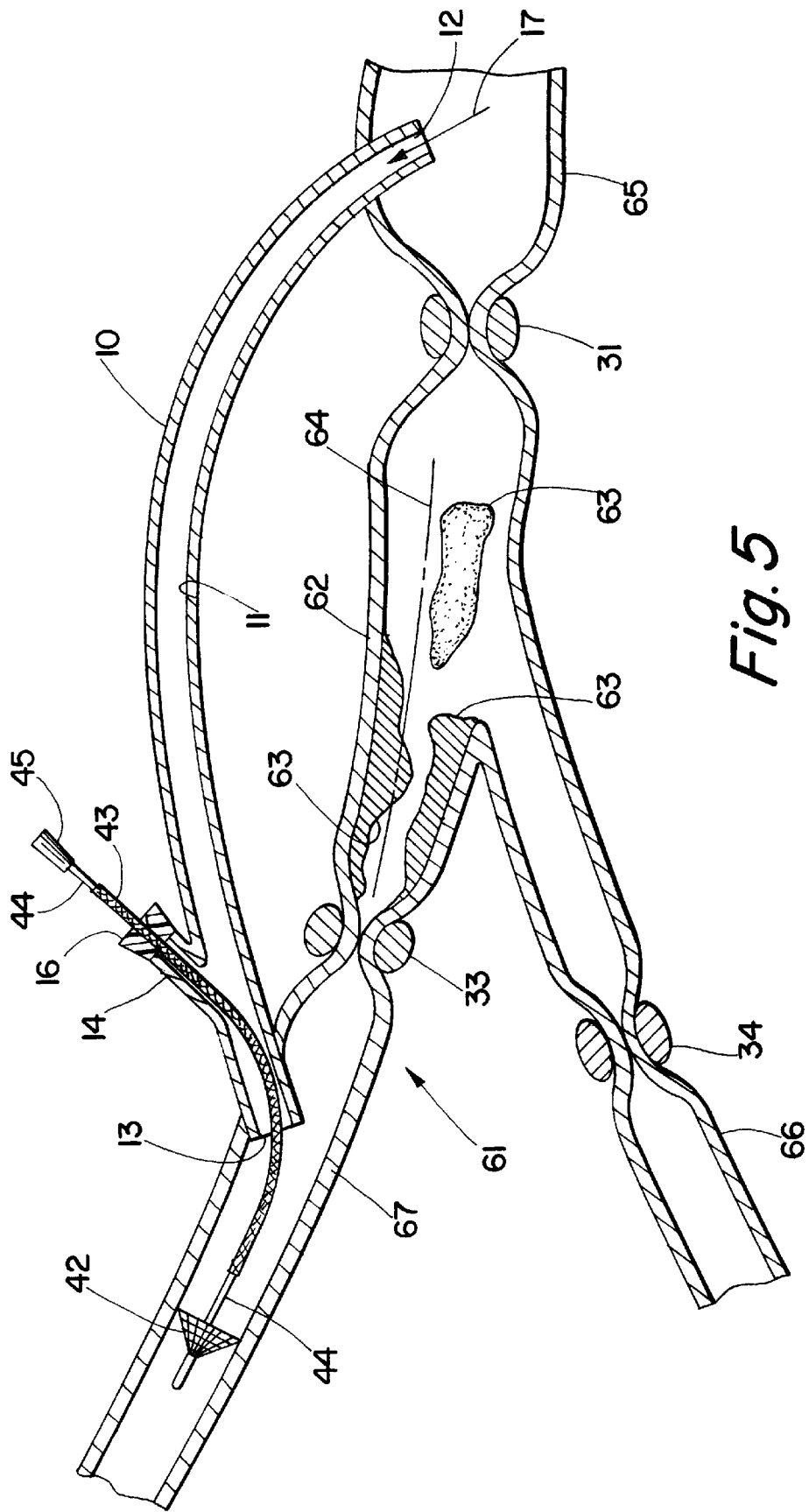
FIG. 5 depicts a non-indwelling shunt bypassing a region of the common and internal carotid arteries during endarterectomy.

In another embodiment, a non-indwelling shunt is used to bypass an endarterectomy region as depicted in FIG. 5. This figure shows common carotid artery 65 which branches into external carotid artery 66 and internal carotid artery 67, and which includes an affected region 62 having atherosclerotic plaque 63 disposed on the lumen thereof. Distal opening 13 of shunt 10 is inserted into vessel 61 through an incision. Back-bleeding through the shunt occurs from the distal opening 13 of lumen 11 in order to purge air from within the shunt. After the shunt is purged, proximal opening 12 is secured by a clamp (not shown). Filter catheter 43 having elongate member 44, filter mesh 42, and control mechanism 45 disposed thereon, is inserted into the lumen of shunt 10 through hemostatic valve 16 and thereafter advanced into the internal carotid artery 67 with filter 42 in a collapsed state. Using control mechanism 45, filter 42 is enlarged to cover substantially all of the cross-sectional area of the internal carotid artery lumen. Proximal opening 12 of shunt 10 is then inserted into common carotid artery 65 through an incision.

With the filter in place, an endarterectomy procedure is conducted on affected region 62 in order to remove deposits 63 as depicted in FIG. 5. This region of the carotid artery is isolated using clamps 31, 33, and 34 as described above, and incision 64 is created to expose plaque deposits 63 within region 62. The plaque is removed, the area is cleaned, the incision is closed, and the clamps are removed in order to purge any remaining gas. The final sutures are then installed to complete the closure of incision 64, and blood flow is reestablished while filter mesh 42 remains in place. This sequence ensures that any remaining debris is captured by filter 42 and is not allowed to enter the brain as emboli. Filter 42 is then collapsed and removed from the internal carotid artery 67 into shunt 10, and thereafter through hemostatic valve 16. Finally, the distal end of the shunt is removed from the internal carotid artery, the incision is sutured, the proximal end of the shunt is removed from the common carotid artery, and the incision in the common carotid artery is sutured. In this manner, the patient is protected from embolization to the brain throughout the arteriotomy procedure.

Referring again to FIG. 4, the introducer sheath 51 will typically have an external diameter of 5–12 French, more preferably 6–8 French. With reference to the filter device, the diameter at the distal end will typically be 1–3 mm, more preferably 1.5–2.5 mm. The filter is generally activated from the proximal end and is deployed from within a small sheath or on the outside of a guidewire or small tube. The length of the filter device is generally 20–40 cm and the deployed diameter of filter mesh 42 will typically be 2 mm or larger, more preferably 4 mm or larger, more preferably 6 mm or larger, more preferably 8 mm or larger, more preferably 10 mm or larger, and generally will be 2–10 mm. The foregoing ranges are set forth solely for the purpose of illustrating typical device dimensions. The actual dimensions of a device constructed according to the principles of the present disclosure may obviously vary outside of the listed ranges without departing from the basic principles disclosed herein.

It will be understood that filtration is an important aspect of the endarterectomy shunt and methods disclosed herein. To filter blood effectively, i.e., to capture embolic material, without unduly disrupting blood flow, the mesh must have the appropriate physical characteristics, including area ($A_M$), thread diameter ($D_T$), and pore size ($S_P$). In the carotid arteries, the mesh 42 must permit flow rates as high as 0.15 L/minute or more, more preferably 0.2 L/minute or more, more preferably 0.25 L/minute or more, more preferably 0.3 L/minute or more, more preferably 0.35 L/minute or more, more preferably 0.4 L/minute or more, more preferably 0.45 L/minute or more, and most preferably 0.5 L/minute or more at pre-filter maximum systolic pressures (proximal to the mesh) of around 200 mm Hg or less.

In order to capture as much of the dislodged material as possible, mesh with the appropriate pore size must be chosen. With reference to embolic material dislodged from the aorta, individual particle diameter ranges from 0.05 mm to 2.88 mm, with a mean diameter of 0.85 mm, and individual particle volume ranges from $6.5 \times 10^{-5}$ mm$^3$ to 12.45 mm$^3$, with a mean particle volume of 0.32 mm$^3$. Approximately 27 percent of the particles have been found to measure 0.6 mm or less in diameter. During cardiac bypass surgery in particular, the total aortic embolic load has been found to range from 570 mm$^3$ to 11200 mm$^3$, with a mean of 3700 mm$^3$, and an estimated cerebral embolic load has been found to range from 60 mm$^3$ to 510 mm$^3$, with a mean of 276 mm$^3$. During carotid endarterectomy, materials dislodged as emboli have similar characteristics to those of aortic materials.

It should also be understood that the embolic material against which the present devices and method protect may include gaseous bubbles inadvertently introduced during the surgical procedure. Air emboli are a common and dangerous occurrence during all types of surgeries. They are potentially most dangerous if allowed to enter the cerebral circulation and cause ischemic events, which may lead to stroke. The type of surgery where this is most likely to occur is surgery on the heart and ascending aorta, but may also occur during endarterectomy. Currently, surgeons make great efforts to de-air and vent the heart and vasculature after a procedure to eliminate air prior to closing the incision and/or taking a patient off of cardiopulmonary bypass. Nevertheless, a small amount of air always remains and is potentially dangerous.

Thus, the filter assembly disclosed herein acts to retain large air bubbles, and under sufficient pressure, causes them to be broken into much smaller bubbles which are much less potentially harmful. A typical pore size for the aortic filter is about 100 μm. When a bubble greater than 100 μm diameter encounters the filter, there must be sufficient pressure on the proximal side of the filter to force the bubble through the pore. The surface tension of the blood generally prevents the bubble from deforming and extruding through the pore, but rather the bubble breaks apart into a plurality of bubbles small enough to pass freely through the pore. The filter thereby acts as a bubble sieve.

The benefit of reducing the size of the interactive bubbles is twofold. First, the potential of a bubble to cause ischemia is directly related to its diameter. The larger the bubble, the more likely it is to block blood flow to a larger area of the brain. Smaller bubbles may block smaller arteries, but will have less overall ischemic effect. Second, smaller bubbles will be absorbed into tissue and cells more quickly than large bubbles, because of their greater surface area to volume ratio. The net effect is smaller bubbles which may make their way into the brain, and bubbles which will be more quickly metabolized further reducing risk of embolic ischemia.

Another method by which large bubbles can be rendered into smaller bubbles is due to velocity and momentum effects. During moments of peak systolic cardiac output, the blood velocity from the heart is at its maximum (100–150 cm/s). If a bubble is trapped against the intraaortic filter and is subject to instantaneous high velocity blood flow, the momentum of the blood on the bubble will cause the bubble to shatter into smaller bubbles. The smaller bubbles will then "escape" through the pores in the filter if they have been rendered small enough.

The area of the mesh required for the device herein, having all of the desirable properties disclosed herein, for use in the carotid arteries is calculated from Bernoulli's equation as described in Barbut et al., U.S. Application Serial No., U.S. application Ser. No. 08/553,137, filed Nov. 7, 1995, now abandoned Barbut et al., U.S. application Ser. No. 08/580,223, filed Dec. 28, 1995, now abandoned Barbut et al., U.S. application Ser. No. 08/584,759, filed Jan. 9, 1996, now abandoned Barbut et al., U.S. application Ser. No. 08/640,015, filed Apr. 30, 1996, now U.S. Pat. No. 5,769,816 and Barbut et al., and U.S. application Ser. No. 08/645,762, filed May 14, 1996. Thus, in one embodiment, a filter for use in the carotid arteries is provided with a mesh having dimensions within the following ranges: mesh area is 10–200 mm$^2$, more preferably 20–150 mm$^2$, more preferably 35–100 mm$^2$, more preferably 50–75 mm$^2$; mesh thickness is 60–280 µm, more preferably 70–270 µm, more preferably 80–260 µm, more preferably 90–250 µm, more preferably 100–250 µm, more preferably 120–230 µm, more preferably 140–210 µm; thread diameter is 30–145 µm, more preferably 40–135 µm, more preferably 50–125 µm, more preferably 60–115 µm, more preferably 70–105 µm; and pore size is 500 µm or less, more preferably 50–180 µm, more preferably 50–170 µm, more preferably 50–160 µm, more preferably 60–150 µm, more preferably 60–140 µm, more preferably 60–130 µm, more preferably 60–120 µm, more preferably 60–110 µm, more preferably 60–100 µm, more preferably 60–90 µm, more preferably 60–80 µm, and usually larger than at least a red blood cell. In a preferred embodiment of the invention, mesh area is 50–75 mm$^2$, mesh thickness is 100–150 µm, thread diameter is 30–100 µm, and pore size is 50–150 µm.

Once appropriate physical characteristics are determined, suitable mesh can be found among standard meshes known in the art. For example, polyester meshes may be used, such as meshes made by Saati Corporation and Tetko Inc. These are available in sheet form and can be easily cut and formed into a desired shape. In a preferred embodiment, the mesh is sonic welded into a cone shape. Other meshes known in the art, which have the desired physical characteristics, are also suitable. Anticoagulants, such as heparin and heparinoids, may be applied to the mesh to reduce the chances of blood clotting on the mesh. Anticoagulants other than heparinoids may also be used, e.g., monoclonal antibodies such as ReoPro (Centocor). The anticoagulant may be painted or sprayed onto the mesh. A chemical dip comprising the anticoagulant also may be used. Other methods known in the art for applying chemicals to mesh may be used.

In an embodiment of the devices suited for placement in the carotid arteries, the expansion frame comprises an inflation seal with inflation system as discussed in U.S. application Ser. Nos. 08/580,223, 08/584,759, 08/640,015, 08/645,762, and 08/683,503. The expansion means, when fully inflated, has a thickness of 0.5–1 mm. The dimensions of the expansion means may be adjusted in alternative embodiments adapted for use in vessels other than the carotid arteries. Alternatively, an expandable frame other than a balloon inflation seal may be used with the devices and methods disclosed herein. Expandable frames include umbrella frames with a plurality of arms as described in U.S. application Ser. Nos. 08/533,137, 08/580,223, and 08/584,759.

All components of this device should be composed of materials suitable for insertion into the body. Additionally, sizes of all components are determined by dimensional parameters of the vessels in which the devices are intended to be used. These parameters are known by those skilled in the art.

Filtration of blood in the carotid arteries will usually be conducted while the heart is functioning normally, i.e., without the use of cardiopulmonary bypass. Thus, blood pressure will be typically 50–200 mm Hg, blood flow will be approximately between 0.15–0.5 L/minute, and the pressure gradient will have no more than a 40 mm Hg drop across the filter when open (i.e., the filter may not be used in some embodiments). Modification of the operational characteristics set forth above for use in vessels other than the carotid arteries are readily ascertainable by those skilled in the art in view of the present disclosure. An advantage of all embodiments including a filter disclosed herein is that both the shunt and filter enter the vessel through a single incision created for the shunt, and therefore the devices and methods herein economize on incisions made in the arteries.

It will also be understood that the filter device may be deployed by insertion through the "Y" arm on the shunt during or after installation in an artery, and for each disclosed method, the shunt and "Y" arm lumens may be common (merging) or separate lumens as depicted in FIG. 1 and FIG. 2, respectively. Moreover, insertion may be made next to the shunt, before, during, or after the shunt is installed. Insertion of the filter device may occur distal to the arteriotomy site, the shunt, and the occlusion clamp through an introducer, either intraoperatively or percutaneously. Where insertion of the filter device occurs percutaneously, distal to the region, the filter device may be inserted and deployed prior to interventional therapy such as arteriotomy, angioplasty, or stent deployment.

Although the foregoing invention has been described in some detail by way of illustration and example for purposes of clarity of understanding, it will be obvious that certain changes and modifications may be practiced which will still fall within the scope of the appended claims. In particular, it should be understood that, although certain features (such as balloon occlusion) are shown by reference to only a single embodiment, those features are applicable to all other embodiments disclosed herein.

What is claimed is:

1. A shunt for maintaining distal blood flow during an arteriotomy procedure, comprising:

a first tubular member having a proximal end, a distal end, and a lumen therebetween, the proximal end having an opening in communication with the lumen, the proximal opening is adapted to receive blood from a first region of an artery, the distal end having an opening in communication with the lumen, the distal opening is adapted to release blood into a second region of the artery;

a second tubular member having a proximal end, a distal end, and a lumen therebetween which merges at an angle of substantially less than 90° and communicates at its distal end with the lumen of the first tubular member, thereby allowing introduction of a medical device into the lumen of the first tubular member;

a hemostatic valve attached to the proximal end of the second tubular member, the valve acting to prevent loss of blood from the lumen of the second tubular member and to permit the introduction of the medical device into the lumens of the second and first tubular members; and a blood filter disposed on an elongated instrument and inserted through the hemostatic valve into the lumen of the second tubular member.

2. A method for maintaining distal blood flow during an arteriotomy procedure, comprising the steps of:

providing a shunt comprising a tubular member having a proximal opening, a distal opening, a first lumen therebetween and a second lumen having a first opening which merges and communicates with the first lumen of the tubular member and a second opening adapted to receive a blood filter device;

inserting the distal opening of the shunt into a first region of a carotid artery and securing the shunt against the lumen of the carotid artery;

inserting the blood filter into the second opening of the second lumen;

advancing the blood filter into and beyond the lumen of the tubular member;

expanding the blood filter to cover a substantial portion of the cross-sectional area of the carotid artery;

inserting the proximal opening into a second region of the carotid artery and securing the shunt against the lumen of the carotid artery; and performing endarterectomy on a region of the carotid artery which lies between the proximal opening and the distal opening of the shunt.

3. The method of claim 2, wherein the blood filter device is deployed after the distal opening and proximal opening are inserted and secured to the carotid artery.

4. The method of claim 2, wherein the blood filter device is inserted into the carotid artery downstream of a bifurcation.

5. The method of claim 2, wherein the blood filter device is deployed before the distal opening and proximal opening are inserted and secured to the artery.

6. The method of claim 2, wherein the proximal opening is inserted and secured to the second region of the artery before the distal opening is inserted and secured to the first region of the artery.

7. The method of claim 2, wherein the step of expanding the blood filter device comprises the step of expanding an inflation seal to which the blood filter is attached.

8. The method of claim 2, wherein the step of securing the shunt against the lumen of the carotid artery includes securing the shunt using a clamp.

9. The method of claim 2, wherein the step of securing the shunt against the lumen of the carotid artery includes securing the shunt using a balloon occluder.

10. A method for maintaining distal blood flow during an arteriotomy procedure, comprising the steps of:

providing a shunt comprising a tubular member having a proximal opening, a distal opening, a first lumen therebetween, and a second lumen having a first segment which lies substantially parallel to the first lumen of the tubular member and a second segment which branches away from the first lumen of the tubular member;

inserting the distal opening of the shunt into a first region of a carotid artery and securing the shunt against the lumen of the carotid artery;

inserting the blood filter into the second segment of the second lumen;

advancing the blood filter into and beyond the first segment of the second lumen;

expanding the blood filter to cover a substantial portion of the cross-sectional area of the carotid artery;

inserting the proximal opening into a second region of the carotid artery and securing the shunt against the lumen of the carotid artery; and performing endarterectomy on a region of the carotid artery which lies between the proximal opening and the distal opening of the shunt.

11. The method of claim 10, wherein the step of expanding the blood filter comprises the step of expanding an inflation seal to which the blood filter is attached.

12. The method of claim 10, wherein the blood filter device is inserted into the carotid artery downstream of a bifurcation.

13. The method of claim 10, wherein the blood filter device is deployed after the distal opening and proximal opening are inserted and secured to the carotid artery.

14. The method of claim 10, wherein the blood filter is deployed before the distal opening and proximal opening are inserted and secured to the artery.

15. The method of claim 10, wherein the proximal opening is inserted and secured to the second region of the artery before the distal opening is inserted and secured to the first region of the artery.

16. The method of claim 10, wherein the step of securing the shunt against the lumen of the carotid artery includes securing the shunt using a clamp.

17. The method of claim 10, wherein the step of securing the shunt against the lumen of the carotid artery includes securing the shunt using a balloon occluder.

* * * * *